United States Patent [19]

Friedmann et al.

[11] Patent Number: 5,026,845

[45] Date of Patent: Jun. 25, 1991

[54] 1,4-DIAZABICYLLO[3.2.2.]NONANE AND INTERMEDIATES FOR THE PREPARATION THEREOF

[76] Inventors: Robert C. Friedmann; John W. Lackey; Brian T. O'Neill, all of Pfizer Inc. 235 E. 42nd St., New York, N.Y. 10017

[21] Appl. No.: 417,120

[22] Filed: Oct. 4, 1989

Related U.S. Application Data

[62] Division of Ser. No. 262,542, Oct. 25, 1988, Pat. No. 4,895,943.

[51] Int. Cl.[5] ............................................. C07D 243/08
[52] U.S. Cl. ..................................... 549/492; 540/575
[58] Field of Search ................................ 540/492, 575

[56] References Cited

U.S. PATENT DOCUMENTS 3,510,437  5/1970  Bonvicini et al. .............. 540/575 X
3,557,086  1/1971  Cantatore et al. .................. 540/575

*Primary Examiner*—Richard L. Raymond

[57] ABSTRACT

Processes and intermediates for preparing 1,4-diazabicyclo[3.2.2.]nonane including a process for the preparation of a compound of the formula

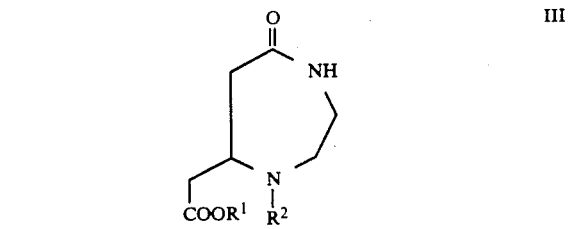

wherein $R^1$ is $C_1$-$C_4$ alkyl or $C_1$-$C_4$ alkyl substituted with 1 to 6 halo groups; and $R^2$ is hydrogen, naphthoyl, substituted naphthoyl, benzyl, substituted benzyl, benzoyl or substituted benzoyl, wherein each of said substituted naphthoyl, substituted benzyl, and substituted benzoyl is substituted with one to three substituents selected from the group consisting of halo, $C_1$-$C_4$ alkoxy and $C_1$-$C_4$ alkyl, comprising reacting a compound of the formula

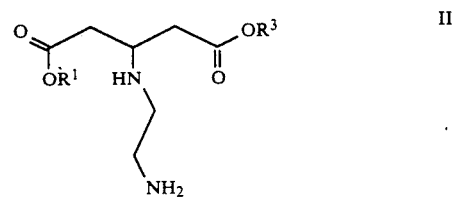

wherein $R^1$ and $R^3$ are independently selected from $C_1$-$C_4$ alkyl and $C_1$-$C_4$ alkyl substituted with 1 to 6 halo groups with an alkyl stannane or a trialkyl aluminum and, if desired, reacting the resulting compound of the formula III wherein $R^2$ is hydrogen with a reagent selected from the group consisting of the optionally substituted reagents naphthoyl chloride, naphthoyl bromide, naphthoyl triflate, benzoyl chloride, benzoyl bromide, benzoyl triflate, benzyl chloride, benzyl bromide and benzyl triflate, wherein the substituents on the substituted naphthoyl, substituted benzyl and substituted benzoyl are as defined above, to prepare the compound of the formula III, as defined above, wherein $R^2$ is other than hydrogen.

13 Claims, No Drawings

1,4-DIAZABICYCLO[3.2.2.]NONANE AND INTERMEDIATES FOR THE PREPARATION THEREOF

This is a division of application Ser. No. 262,542, filed on Oct. 25, 1988, now U.S. Pat. No. 4,895,943.

BACKGROUND OF THE INVENTION

The present invention relates to processes and intermediates for the preparation of 1,4-diazabicyclo[3.2.2-]nonane.

The latter compound, which is disclosed in *Zhurnal Obshchei Khimii*, 33 (7), 2167–2172 (1963), is useful in preparing the antibacterial compound 7-(1,4-diazabicyclo[3.2.2]non-4-yl)-1-ethyl-6-fluoro-1,4-dihydro-4-oxo-3-quinolinecarboxylic acid methane sulfonate salt. Said antibacterial compound is disclosed in U.S. Pat. No. 4,775,668. Other quinolinecarboxylic acids that may be similarly reacted with 1,4-diazabicyclo[3.2.2]nonane to prepare antibacterial compounds are disclosed in U.S. Pat. No. 4,571,396.

SUMMARY OF THE INVENTION

The present invention relates to a process for the preparation of a compound of the formula

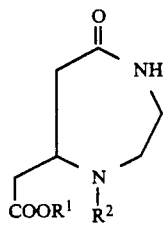

III wherein $R^1$ is $C_1$–$C_4$ alkyl or $C_1$–$C_4$ alkyl substituted with 1 to 6 halo groups; and $R^2$ is hydrogen, naphthoyl, substituted naphthoyl, benzyl, substituted benzyl, benzoyl or substituted benzoyl, wherein each of said substituted naphthoyl, substituted benzyl, and substituted benzoyl is substituted with one to three substituents selected from the group consisting of halo, $C_1$–$C_4$ alkoxy and $C_1$–$C_4$ alkyl, comprising reacting a compound of the formula

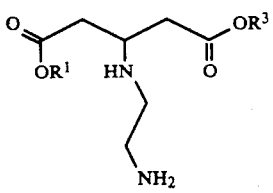

II wherein $R^1$ and $R^3$ are independently selected from $C_1$–$C_4$ alkyl and $C_1$–$C_4$ alkyl substituted with 1 to 6 halo groups with an alkyl stannane or a trialkyl aluminum and, if desired, reacting the resulting compound of the formula III wherein $R^2$ is hydrogen with a reagent selected from the group consisting of the optionally substituted reagents naphthoyl chloride, naphthoyl bromide, naphthoyl triflate, benzoyl chloride, benzoyl bromide, benzoyl triflate, benzyl chloride, benzyl bromide and benzyl triflate, wherein the substituents on the substituted naphthoyl, substituted benzyl and substituted benzoyl are as defined above, to prepare the compound of the formula III as defined above, wherein $R^2$ is other than hydrogen. As used herein, and unless indicated otherwise, halo includes fluoro, chloro, bromo and iodo. In a preferred embodiment of the invention, $R^1$ and $R^3$ are the same. In another preferred embodiment of the invention $R^2$ is benzoyl. More preferably, $R^1$ and $R^3$ are the same and $R^2$ is benzoyl. The preferred reagents for preparing compounds of the formula III wherein $R^2$ is other than hydrogen are the aforementioned chlorides. The most preferred reagent is benzoyl chloride.

The present invention also relates to a process for preparing a compound of the formula

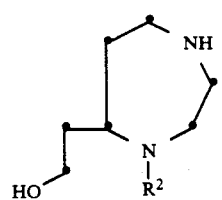

V wherein $R^2$ is naphthoyl, substituted naphthoyl, benzyl, substituted benzyl, benzoyl or substituted benzoyl, wherein each of said substituted naphthoyl, substituted benzyl, and substituted benzoyl is substituted with one to three substituents selected from the group consisting of halo, $C_1$–$C_4$ alkoxy and $C_1$–$C_4$ alkyl, comprising reducing a compound of the formula

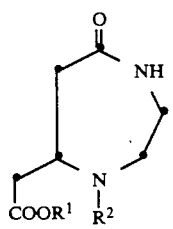

IV wherein $R^1$ is as defined above and $R^2$ is as defined with respect to formula V.

It should be understood that as a consequence of the foregoing reduction reaction, the benzoyl group and the substituted benzoyl group may be reduced, respectively, to a benzyl group and a substituted benzyl group and the naphthoyl group and the substituted naphthoyl group may be reduced, respectively, to a methylnaphthyl group and a substituted methylnaphthyl group.

The present invention also relates to a process for preparing a compound of the formula

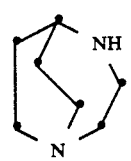

VIII comprising reacting a compound of the formula V, as defined above, with a reagent, such as thionyl chloride or thionyl bromide, that is capable of replacing the hydroxy group by a leaving group, such as chloro or bromo, effecting ring closure with a base, and then replacing the optionally substituted benzyl, optionally substituted methylnaphthyl or optionally substituted benzoyl group with hydrogen.

The present invention also relates to a compound of the formula

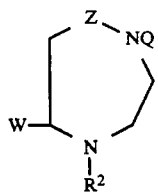

wherein Z is C=O or CH$_2$, R$^2$ is hydrogen, naphthoyl, substituted naphthoyl, benzyl, substituted benzyl, benzoyl or substituted benzoyl, wherein each of said substituted naphthoyl, substituted benzyl, and substituted benzoyl is substituted with one to three substituents selected from the group consisting of halo, C$_1$-C$_4$ alkoxy and C$_1$-C$_4$ alkyl, Q is hydrogen, and W is —CH$_2$CH$_2$OH, —CH$_2$CH$_2$X or —CH$_2$COOR$^1$ wherein R$^1$ is C$_1$-C$_4$ alkyl or C$_1$-C$_4$ alkyl substituted with 1 to 6 halo groups, and X is a leaving group (e.g., chloro or bromo) or OH, or W and Q form an alkylene bridge of the formula —CH$_2$CH$_2$—, with the proviso that Z is C=O when W is —CH$_2$COOR$^1$ and Z is CH$_2$ when W is —CH$_2$CH$_2$OH or —CH$_2$CH$_2$X or when W and Q form said alkylene bridge. Preferred leaving groups are chloro and bromo, the most preferred leaving group being chloro.

DETAILED DESCRIPTION OF THE INVENTION

As used herein, the term "halo" includes fluoro, chloro, bromo and iodo. Generally, fluoro, chloro and bromo are preferred.

The following reaction scheme illustrates the processes of the present invention.

Scheme 1

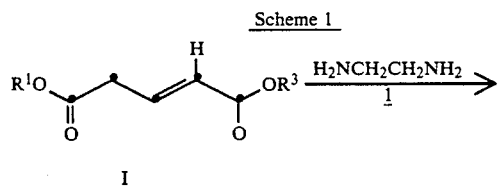

I

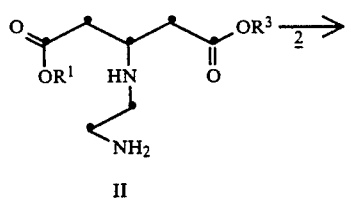

II

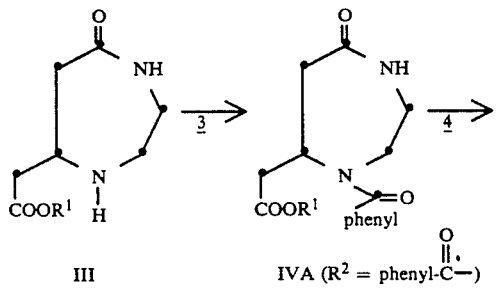

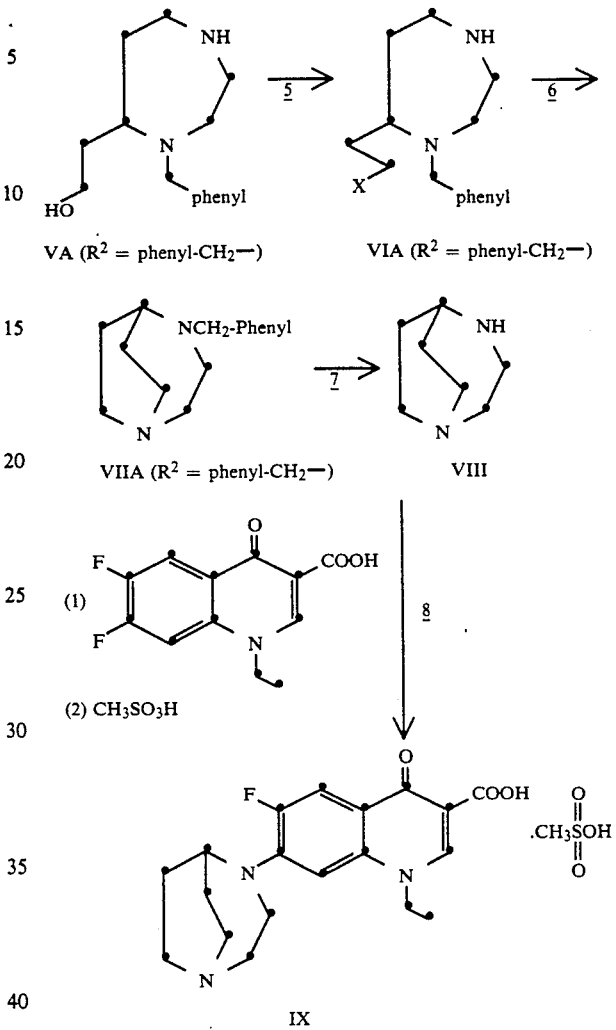

In reaction 1 of Scheme 1, a compound of the formula I wherein R$^1$ and R$^3$ are independently selected from C$_1$-C$_4$ alkyl and C$_1$-C$_4$ alkyl substituted with 1-6 halo groups is reacted with H$_2$NCH$_2$CH$_2$NH$_2$ to prepare a compound of the formula II. Preferably, R$^1$ and R$^3$ are the same so that two products do not form in step 2. The solvent should be an inert solvent. Suitable solvents include 1,2 ethylenediamine, tetrahydrofuran, diethylether, dioxane, dimethoxyethane, benzene, toluene and dimethylformamide. The reaction temperature is not critical but will generally be in the range of about 10° C. to about 45° C. with 25° C. being optimum. The compound of the formula I wherein both R$^1$ and R$^3$ are ethyl is available from Aldrich Chemical Company. Other compounds of the formula I may be prepared as follows:

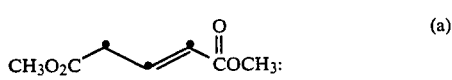  (a)

prepared from readily available 1,3-dimethylacetone dicarboxylate by catalytic reduction to the alcohol by the procedure of Lochte (*J. Amer. Chem. Soc.* 68, 721 (1946)) and elimination of the corresponding mesylate with base.

(b) wherein Ph is phenyl:

prepared from commercially available glutaconic acid and phenol through reactions with dicyclohexyl carbodimide and dimethylaminopyridine.

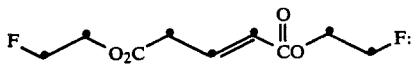
(c)

prepared from commercially available glutaconic acid and fluoroethanol through reaction with dicyclohexyl carbodimide and dimethylaminopyridine.

(d)

As above from glutaconic acid and trifluoroethanol.

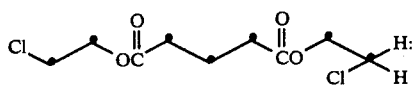
(e)

As above from glutaconic acid and chloroethanol

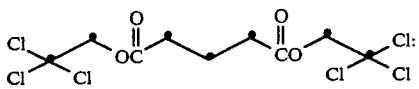
(f)

As above from glutaconic acid and trichloroethanol.

In reaction 2 of Scheme 1, a compound of the formula II is reacted in an inert solvent with an alkyl stannane, such as tri-n-butyltin triflate, mesylate, tosylate or halide, or with a trialkyl aluminum such as trimethylaluminum, or with triethylaluminum or triisobutylaluminum. Of the foregoing alkyl stannanes, the tri-n-butyltintriflate is the most reactive. This compound was prepared by the procedure of Corey (*Tetrahedron Letters*, 2419 (1984). Suitable solvents include tetrahydrofuran, dimethoxyethane and dioxane. The reaction temperature is not critical but will generally be in the range of about 55° to about 100° C., with 67° C. being optimum. Each of the alkyl groups of the stannane will preferably have about one to about ten carbon atoms, more preferably about one to about four carbon atoms. The alkyl groups of the trialkylaluminum will preferably have about one to about ten carbon atoms with trimethylaluminum being preferred. This material can be purchased from the Aldrich Chemical Co. as a solution in toluene or as the neat reagent. The product (III) of reaction 2 is not generally isolated but is carried directly into reaction 3.

In reaction 3 of Scheme 1, a compound of the formula III is reacted in an inert solvent in the presence of an organic base such as triethylamine or dimethylaminopyridine or a mixture of the foregoing bases with a reagent selected from the group consisting of optionally substituted naphthoyl chloride, naphthoyl bromide, naphthoyl triflate, benzoyl chloride, benzoyl bromide, benzoyl triflate, benzyl chloride, benzyl bromide and benzyl triflate, wherein the substituents on the substituted naphthoyl, substituted benzyl and substituted benzoyl are as defined above. Preferably, an excess of such reagent is used. Suitable solvents include tetrahydrofuran, dimethoxyethane, dioxane and methylene chloride. The reaction temperature is not critical but will generally be in the range of about −10° C. to about 25° C., preferably about 0° C. The specific nitrogen protecting group illustrated in formula IVA is benzoyl. If desired, one of the other protecting groups mentioned above can be substituted for the benzoyl group.

The product from reaction 3 when the nitrogen is protected by benzoyl is isolated by chromatography on silica gel to remove residual alkyl tin oxides. Alternatively, one ay employ the method of Jacobus (*J. Org. Chem.*, 44, 449 (1979)) by dissolving the crude oily product in methanol and treating the solution with an aqueous solution of potassium fluoride. The trialkyl tin fluoride which precipitates is removed by filtration and the desired product is obtained after evaporation of the solvent and crystallization from methylene chloride and ethyl ether. Alternatively, residual tin oxides may be removed by extraction with aqueous ammonium hydroxide solution.

In reaction 4 of Scheme 1, a compound of the formula IVA is reacted with a reducing agent to obtain a compound of the formula VA. Suitable reducing agents include lithium aluminum hydride, Vitride (trademark) (a solution of sodium bis(2-methoxyethoxy)aluminum hydride in toluene), borane in tetrahydrofuran (THF), borane in dimethylsulfide, and diisobutylaluminum hydride (dibal). The solvent should either be inert or it should function as or assist in the functioning of the reducing agent. The optimum solvent will depend on the reducing agent chosen. In general, etheral solvents such as THF, ether or dimethoxyethane are preferred. The reaction may also be conducted in toluene, benzene or hexane when Vitride (trademark) or dibal is used.

It should be noted that the benzoyl nitrogen protecting group of the compound of formula IVA is reduced to a benzyl group in reaction 4 but that the latter group continues to function as a nitrogen protecting group.

In reaction 5 of Scheme 1, a compound of the formula VA is reacted with a reagent capable of converting the hydroxy group to a leaving group, designated by X in the compound of the formula VIA. The foregoing reaction may be conducted in an inert solvent. The preferred solvent will be selected based on the choice of the desired leaving group. In general, suitable solvents include dichloroethane, toluene, and benzene. Alternatively, the solvent can serve as the halogenation agent. The reaction temperature is not critical but will generally be in the range of about 70° to about 120° C.

For the compound of the formula VIA, the preferred leaving group is chloro. Said chloro group may be introduced by reacting the compound of the formula VA with neat SOCl₂ at elevated temperature to form a compound of the formula VI wherein X is chloro. The temperature for this reaction is not critical but will generally be in the range of about 75° to about 85° C.

In reaction 6 of Scheme 1, ring closure is effected by reacting the compound of formula VIA in an inert solvent with a nonnucleophilic base. If aqueous base is used, the base must be concentrated in order to avoid dissolving the water soluble product. Suitable bases include alkaline hydroxides (e.g., sodium and potassium hydroxide). Suitable solvents include water. The preferred reagent for effecting ring closure is 50% aqueous sodium hydroxide. The temperature of reaction 6 is not critical but will generally range from about 15° C. to about 35° C. When ring closure is effected with 50% aqueous sodium hydroxide, the preferred temperature range is about 20 to 25° C.

After ring closure, the protecting group on the nitrogen of the compound of the formula VIIA is removed by standard techniques to yield the compound of formula VIII. Such removal of the protecting group may be by hydrogenation at a temperature of about 55° C. to 75° C. using Pd(OH)$_2$ as the catalyst. The pressure is preferably about 3 to about 6 atmospheres. Suitable solvents include alcohols (e.g., C$_1$–C$_4$ alcohols). A preferred solvent is methanol. Other suitable hydrogenation catalysts include palladium on carbon.

The pressure of the foregoing reactions is generally not critical. Except for the hydrogenation reaction discussed above, the pressures of the foregoing reactions should preferably be in the range of about 0.5 to about 2 atmospheres, more preferably ambient pressure (i.e. about 1 atmosphere).

In reaction 8, the compound of the formula VIII is reacted with 1-ethyl-6,7-difluoro-1,4-dihydro-4-oxo-3quinoline carboxylic acid as described in European Patent Application Publication Number 0215650 to form 7-(1,4-diazabicyclo[3.2.2]non-4-yl)-1-ethyl-6-fluoro1,4-dihydro-4-oxo-3-quinolinecarboxylic acid methane sulfonate salt, which may be represented by formula IX.

The following Examples illustrate the processes of the present invention. All melting points referred to in the Examples are uncorrected.

EXAMPLE 1

Diethyl-3-amino[N-2-aminoethyl]-1,5-pentanedicarboxylate

To 7.15 ml (0.107 mole) of ethylenediamine at room temperature and under a nitrogen atmosphere was added diethylglutaconate 1.89 ml (0.0107 mole) dropwise over 5 minutes. The mixture was stirred at room temperature for 15 minutes and then evaporated in vacuo. There was obtained 2.6 g (100% yield) of the title compound which was used directly in the following step. $^1$H NMR(CDCl$_3$, 300MHz)δ4.1 (4H, q, J=9 Hz), 3.34 (1H, m), 2.7 (4H, m), 2.47 (4H, d, J=6 Hz), 1.68 (3H, brs), 1.22 (6H, t, J=9 Hz).

EXAMPLE 2

Ethyl-4-benzoyl-5-(2-ethanoic acid)-1,4-diazepin-7-one

To a 500 ml three neck round bottom flask under nitrogen atmosphere was charged 8.37 g (0.034 mole) of the crude product from Example 1 and 185 ml of anhydrous THF (tetrahydrofuran). To the resulting clear solution, which was cooled to 0° C., was added a solution of 15 g (0.034 mole) of tri-n-butyltintrifluoromethanesulfonate (E.J. Corey, Tetrahedron Letters, 2419 (1984)) in 50 ml of anhydrous THF. The addition took 5 minutes and no exotherm was observed. The reaction mixture was then heated under reflux for a period of 18 hours. To this solution, which was again cooled to 0° C., was charged 9.48 ml (0.068 m) of triethylamine, 0.34 g (0.0068 mole) of N,N-dimethylaminopyridine and 7.93 ml (0.068 mole) of benzoyl chloride. The latter reagent was added over 5 minutes with the formation of precipitated triethylamine hydrochloride. The slurry was stirred for 2.5 hours while warming to room temperature. This mixture was then evaporated to a crude residue which was chromatographed directly on silica gel (Woelm (trademark) 32-63 m) with 10% methanol in ethyl acetate. There was obtained 8.1 g (78%) of the title compound (mp 158°-159° C.); $^1$H NMR (DMSO-360° K., 250 MHz δ: 7.42 (5H, m), 4.85 (1H, br), 4.10 (2H, dq, J=9Hz), 3.21 (1H, m), 3.05 (4H, s), 2.90 (1H, dd, J=5 Hz), 2.65 (2H, ddd, J=15 Hz, J=7 Hz, J=6 Hz), 2.45 (1H, dd, J=15 Hz, J=6 Hz), 1.15 (3H, t, J=9 Hz); IR (CHC13) 3410, 2960, 2920, 1730, 1670, 1630, 1440 1200 cm$^{-1}$; HRMS m/e calculated for C$_{16}$H$_{20}$N$_2$O$_4$:304.1423, found : 304.1386.

Similarly prepared were the following:
ethyl-4-[4-bromobenzoyl]-5-(2-ethanoic acid) 1,4-diazepin-7-one, mp 158°-162°;
ethyl-4-[1-napthoyl]-5-(2-ethanoic acid)-1,4-diazepin-7-one, mp 145°-150° C.;
ethyl-4-[2-napthoyl]-5-(2-ethanoic acid)-1,4-diazepin-7-one, mp 185°-190° C.;
ethyl-4-[2-napthoyl]-5-(2-ethanoic acid)-1,4-diazepin-7-one, mp 144°-145° C.; and
ethyl-4-carbobenzyloxy-5-(2-ethanoic acid)-1,4-diazepin-7-one, oil.

EXAMPLE 3

4-Phenylmethyl-5-(2-hydroxyethyl)-1,4-diazepine

To a 1 liter 3-neck flask equipped with a magnetic stir bar, condenser, dropping funnel, and nitrogen inlet was charged 210 ml (0.210 mole) of 1.0 M lithium aluminum hydride in THF solution. At room temperature, a solution of the above described compound (8.0 g (0.026 mole)) in 100 ml of THF was added over 15 minutes with the evolution of a gas from the reaction mixture. When the gas evolution ceased (15-20 minutes), the reaction mixture was heated under reflux for a period of 18 hours. The mixture was allowed to cool to room temperature and was then quenched in the following manner: 8 ml of water was added dropwise over 30 minutes producing a strong exotherm. The resulting slurry was then treated with 8 ml of 15% (w/w) aqueous sodium hydroxide. To this mixture was added 24 ml of water and the mixture was then stirred for an additional 15 minutes, subsequently filtered, and the filtrate was concentrated to an oil. There, was obtained 5.65 g (100%) of the title compound. This material was satisfactory for further synthetic use without purification. However, a small sample was purified by silica gel chromatography for analysis (CHCl$_3$ EtOH: aqueous NH$_4$OH; 9.0: 0.6: 0.4). 1H NMR (CDCl$_3$, 300MHz)δ:7 26 (5H, m), 3.78 (5H, m), 3.28 (1H, m), 2.88 (6H, br m), 2.66 (1H, m), 1.84 (3H, br m), 1.47 (1H, m); C$^{13}$NMR (CDCl$_3$, 75.43 MHz)δ:138.7, 129.0, 128.4, 127.1, 62.9, 61.9, 52.9, 51.8, 47.1, 46.9, 35.4, 33.8; IR (neat) 3300, 2920, 1735, 1450, 1360, 1240, 1050 cm$^{-1}$:HRMS m/e calculated for C$_{14}$H$_{22}$N$_2$O:234.1733, found 234 1695.

EXAMPLE 4

4-Phenylmethyl-5-(2-chloroethyl)-1,4-diazepinedihydrochloride

To a round bottomed flask equipped with a magnetic stir bar, condenser and calcium sulfate drying tube was charged 1.3 g (0.0055 mole) of the product from the previous step and the system was cooled to 0° C. To the oil was added 4.86 ml (0.066 mole) of thionyl chloride. The dark reaction mixture was allowed to warm slowly to room temperature and was then heated under reflux for 1 hour. The mixture was allowed to cool to room temperature and was then carefully quenched with 30 ml of water by dropwise addition. The resulting solution was treated with 3 g of activated charcoal and heated to 70° C. for 1 hour. The hot solution was filtered through diatomaceous earth (Celite (trademark)) and the filtrate was concentrated to dryness. This was done with the aid of a small amount (about 10 ml) of ethanol to help remove the last traces of water. The title compound was obtained as a foam in 64% yield (1.43 ). This material was used without further purification HRMS m/e calculated for $C_{14}H_{21}N_2Cl$:252.1393, found 252 1281.

EXAMPLE 5

4-Phenylmethyl-1,4-diazabicyclo[3.2.2]nonane

To a 250 ml 3-neck flask round bottom flask under nitrogen was added the product from the previous reaction (1.43 g, 0.0036 mole) and 12 ml of 50% sodium hydroxide in water. The mixture was stirred for 1 hour and was then extracted with 3 times 50 ml methylene chloride. The organic layer was washed with brine and then dried over sodium sulfate. After concentration there was obtained 0.7 g (90%) of the title product. This material was used in the next steP without further purification. $^1$H NMR (CDCl$_3$, 250 MHz)$\delta$:7.30 (5H, m), 3.65 (2H, s), 3.00 (6H, m), 2.89 (1H, m), 2.70 (2H, t, J=6.2 Hz), 1.95 (2H, m), 1.6 (2H, m);$C^{13}$NMR(CDCl$_3$, 62.9 MHz) 139.67, 128.70, 128.29, 126.91, 61.89, 55.43, 52.70, 51.00, 46.92, 25.61; HRMS m/e calculated for $C_{14}H_{20}N_2$:216.1628, found 216 1620.

EXAMPLE 6

1,4-Diazabicyclo[3.2.2]nonaneditosylate salt

To a methanol solution of 0.5 g 0.0023 mole) of the product from the previous reaction was added 0.1 g palladium hydroxide catalyst (20% on carbon). The mixture was placed under 50 psi hydrogen pressure, was heated to 65° C. and hydrogenated in a Parr apparatus for a total of 18 hours. During this time, one catalyst recharge was conducted. The reaction mixture was filtered through Celite (trademark) and evaporated. The resulting oil (0.222 g) could be used to prepare 7-(1,4-diazabicyclo[3.2.2]non-4-yl)-1-ethyl-6-fluoro1,4-dihydro-4-oxo-3-quinolinecarboxylic acid methane sulfonate without further purification. However, for characterization purposes, it was dissolved in 2.0 ml of isopropanol and was treated with 1.5 g (0.0077 mole) of toluene sulfonic acid in 2.5 ml of isopropanol. A precipate formed immediately and was collected after the slurry was cooled to 0° C. The title compound was obtained in 51% overall yield (0.6 g). $^1$H NMR(DMSO, 300MHz) $\delta$7.49 (2H, d, J=9 Hz), 7.11 (2H, d, J-9 Hz), 3.96 (1H, br. t), 3.54 (4H, m), 3.43 (4H, m), 3.31 (2H, m),2.28 (3H, s), 2.19 (2H, m); $C^{13}$(DMSO, 75.43 MHz) $\delta$1.44.7, 138.4, 128.4, 125.5, 50.1, 46.9, 44.8, 37.3, 20.8, 19.8; HRMS m/e calculated for $C_7H_{14}N_2$:126.1158, found :126.1158.

We claim:

1. A compound of the formula

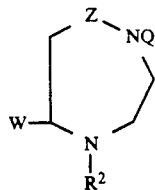

wherein Z is C=O or $CH_2$, $R^2$ is hydrogen, naphthoyl, substituted naphthoyl, benzyl, substituted benzyl, benzoyl or substituted benzoyl, wherein each of said substituted naphthoyl, substituted benzyl, and substituted benzoyl is substituted with one to three substituents selected from the group consisting of halo, $C_1$-$C_4$ alkoxy and $C_1$-$C_4$ alkyl, Q is hydrogen, and W is —$CH_2CH_2OH$, —$CH_2CH_2X$ or —$CH_2COOR^1$ wherein $R^1$ is $C_1$-$C_4$ alkyl or $C_1$-$C_4$ aklyl substituted with 1 to 6 halo groups, and X a leaving group with the proviso that Z is C=O when W is —$CH_2COOR^1$ and Z is $CH_2$ when W is —$CH_2CH_2OH$ or —$CH_2CH_2X$.

2. A compound according to claim 1, said compound having the formula

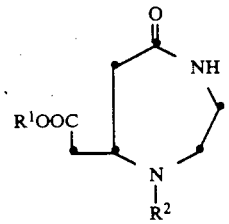

wherein $R^1$ is $C_1$-$C_4$ alkyl or $C_1$-$C_4$ alkyl substituted with 1 to 6 halo groups and $R^2$ is as defined in claim 1 but is other than hydrogen.

3. A compound according to claim 2, wherein $R^1$ is ethyl.

4. A compound according to claim 2, wherein $R^2$ is benzoyl.

5. A compound according to claim 4 wherein $R^1$ is ethyl.

6. A compound according to claim 1, said compound having the formula

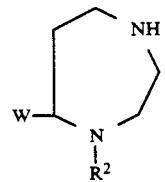

wherein W is as defined in claim 1 and $R^2$ is as defined in claim 3 but is other than hydrogen.

7. A compound according to claim 6, wherein $R^2$ is benzyl.

8. A compound according to claim 6, wherein W is —$CH_2CH_2OH$.

9. A compound according to claim 6, wherein W is —$CH_2CH_2X$ wherein X is a leaving group.

10. A compound according to claim 9, wherein X is Cl.

11. A compound according to claim 7, wherein W is —$CH_2CH_2OH$.

12. A compound according to claim 7, wherein W is —$CH_2CH_2X$ wherein X is a leaving group.

13. A compound according to claim 12, wherein X is Cl.

* * * * *